US00PP34657P2

(12) United States Plant Patent
Worrell et al.

(10) Patent No.: US PP34,657 P2
(45) Date of Patent: Oct. 18, 2022

(54) GROUND COVER ROSE PLANT NAMED 'MEIJOVAUX'

(50) Latin Name: *Rosa hybrida*
Varietal Denomination: MEIJOVAUX

(71) Applicant: THE CONARD PYLE COMPANY, West Grove, PA (US)

(72) Inventors: Rick Worrell, Plant City, FL (US); Kristen Smith, West Grove, PA (US)

(73) Assignee: The Conard Pyle Company, West Grove, PA (US)

( * ) Notice: Subject to any disclaimer, the term of this patent is extended or adjusted under 35 U.S.C. 154(b) by 30 days.

(21) Appl. No.: 17/565,663

(22) Filed: Dec. 30, 2021

(30) Foreign Application Priority Data

Apr. 21, 2021 (QZ) ..... PBR 2021/1085

(51) Int. Cl.
*A01H 5/02* (2018.01)
*A01H 6/74* (2018.01)

(52) U.S. Cl.
USPC ..... Plt./101

(58) Field of Classification Search
USPC ..... Plt./101
See application file for complete search history.

(56) References Cited

U.S. PATENT DOCUMENTS

PP17,877 P3 7/2007 Meilland
PP18,874 P2 6/2008 Meilland

OTHER PUBLICATIONS

CPVO Variety Data Sheet 2021.*

* cited by examiner

*Primary Examiner* — Annette H Para
(74) *Attorney, Agent, or Firm* — Panitch Schwarze Belisario & Nadel LLP; Stephany G. Small; Travis W. Bliss

(57) ABSTRACT

A new and distinct variety of rose plant, referred to by its cultivar name, 'MEIJOVAUX', is disclosed. The new variety forms attractive, semi-double creamy pink with a creamy yellow center colored flowers. Attractive rather dense with a semi-glossy aspect foliage is formed, which contrasts beautifully with the blossoms. A ground cover growth habit is displayed. The new variety is well suited for providing attractive ornamentation in the landscape.

1 Drawing Sheet

Latin name of genus and species of plant claimed: *Rosa hybrida.*

Variety denomination: 'MEIJOVAUX'.

CROSS REFERENCE TO RELATED APPLICATIONS

This application claims priority to Plant Breeders' Right Application Number 2021/1085, which was filed at Community Plant Variety Office in the European Union on Apr. 21, 2021, the contents of which are hereby incorporated by reference for all purposes.

BACKGROUND OF THE INVENTION

The new variety of *Rosa hybrida* plant of the present invention was discovered as a spontaneous mutation in a single cutting of the variety 'MEIJOCOS' (U.S. Plant Pat. No. 18,874) in December 2015 in Park City, Fla., United States of America as a spontaneous mutation from a single cutting. The new variety was selected and preserved primarily because of its color difference from the 'MEIJOCOS' parent variety.

The parentage of the new variety can be summarized as follows:

spontaneous mutation in a single cutting of 'MEIJOCOS'

The new variety has been found to undergo asexual propagation in West Grove, Pa. by a number of routes, including softwood cuttings. Asexual propagation by the above-mentioned techniques in West Grove, Pennsylvania has shown that the characteristics of the new variety are stable and are strictly transmissible by softwood cuttings asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) provides a ground cover growth habit with procumbent vegetation,
(b) forms semi-double creamy pink with a creamy yellow center colored flowers, and
(c) exhibits a semi-glossy foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'MEIJOCOS' variety (i.e., the parent variety) displays deep pink with a white center colored flowers, whereas the new variety displays creamy pink with a creamy yellow center colored flowers. Moreover, the new variety can be readily distinguished from other similar non-parental varieties. For example, the 'MEIGALPIO' variety (U.S. Plant Pat. No. 17,877) displays smaller sized flowers compared to the flowers of new variety.

The new variety has been named 'MEIJOVAUX'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one year of age and were observed during September while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—reverse.

Element 7—illustrates a specimen of an open flower—plan view—observe.

Element 8—illustrates a specimen of fully open flowers—plan view—reverse.

Element 9—illustrates a specimen of fully open flowers—plan view—observe.

Element 10—illustrates a specimen of a floral receptacle showing arrangement of the pistils.

Element 11—illustrates a specimen of a floral receptacle showing arrangement of the stamens and pistils (stamens removed).

Element 12—illustrates a specimen of a flowering stem.

Element 13—illustrates a specimen of a leaf with 7 leaflets—plan view—upper surface.

Element 14—illustrates a specimen of a leaf with 5 leaflets—plan view—upper surface.

Element 15—illustrates a specimen of a leaf with 3 leaflets—plan view—upper surface.

Element 16—illustrates a specimen of a leaf with 7 leaflets—plan view—under surface.

Element 17—illustrates a specimen of a leaf with 5 leaflets—plan view—under surface.

Element 18—illustrates a specimen of a leaf with 3 leaflets—plan view—under surface.

DETAILED BOTANICAL DESCRIPTION

The chart used in the identification of the colors is that of The Royal Horticultural Society (R.H.S. Colour Chart, 2001 edition), London, England. The terminology which precedes reference to the chart has been added to indicate the corresponding color in more common terms. The description is based on the observation of one-year-old specimens of the new variety during September while budded on their own roots and growing outdoors at Le Cannet des Maures, Var, France.

Commercial classification: Ground Cover Rose Plant.

Plant:

*Habit*.—Ground cover.

*Height*.—Typically 20 to 40 cm on average.

*Width*.—Typically 50 to 70 cm on average.

Branches:

*Color*.—Young stems: commonly near a color between Green Group 143B and Green Group 143C. — adult wood: commonly near Yellow-Green Group 146B.

*Length*.—From the crown to the flower is approximately between 20 to 40 cm on average.

*Diameter*.—Approximately between 0.3 to 0.6 cm on average.

*Young shoots*.—Anthocyanin coloration: commonly near Greyed-Red Group 178A.

*Thorns*.—Configuration on adult stems: rather upright and rather elongated on the upper surface and slightly concave on the under surface. — long prickles — quantity: commonly approximately 5 thorns per 10 cm long young stem and commonly approximately 5 thorns per 10 cm long adult stem. — long prickles— base shape: narrow obovate. — long prickles— size: approximately 0.7 cm in length on average on young stems and on adult stems. — long prickles— color: commonly near Yellow-Green Group 146D on young stems, and commonly near Greyed-Orange Group 165A on adult stems. — small prickles— quantity: absent.

*Internode*.—Numbers on the entire branch: approximately between 5 to 8 on average. — length: approximately between 3.0 to 4.0 cm on average.

Foliage:

*General appearance*.—Rather dense with semi-glossy aspect.

*Number of leaflets*.—3, 5, 7; most often 7.

*Terminal leaflet*.—Length: approximately 3.5 cm on average. — width: approximately 1.5 cm on average.

7 *leaflets leaf*.—Length: approximately 10.0 cm on average. — width: approximately 5.0 cm on average.

*New foliage*.—Upper surface color: commonly near Green Group 141A. — under surface color: commonly near Green Group 137D. — anthocyanin coloration: absent.

*Adult foliage*.—Upper surface color: commonly near Green Group 137A. — under surface color: commonly near Green Group 137C. — anthocyanin coloration: absent.

Leaflets:

*Shape*.—Tip: acute. — base: obtuse.

*Glossiness of upper surface*.—Medium.

*Texture*.—Thick.

*General appearance*.—Oblong.

*Serration*.—Small and single.

*Undulation on the margin*.—Medium.

*Venation*.—Color is commonly near a color between Green Group 143A and Green Group 143B and pattern is impary pinnate.

*Petiole rachis*.—Color of upper surface: commonly near a color between Green Group 143A and Green Group 143B. — color of under surface: commonly near Yellow-Green Group 144B. — texture: upper surface is little glandular, under surface has few prickles. — rachis of terminal leaflet: length is 4.5 cm on average, and diameter is approximately 0.1 cm on average.

*Petioles*.—Upper surface: little glandular. — under surface: few prickles. — color of upper surface: commonly near a color between Green Group 143A and Green Group 143B. — color of under surface: commonly near Yellow-Green Group 144B. — length: approximately between 2.0 to 3.5 cm on average. — diameter: approximately 0.1 cm on average

*Stipules*.—General appearance: adnate, pectinate and narrow. — length: approximately 1.8 cm on average. — width: approximately 0.5 cm on average. — color of upper surface: commonly near Yellow-Green Group 146C. — color of under surface: commonly near Yellow-Green Group 146D.

Inflorescence:

*Number of flowers per stem*.—Typically 40 to 70 flowers per stem.

*Lastingness of the bloom*.—On the plant: approximately 7 days on average. — in vase: not applicable.

*Bud*.—Shape: conical. — size: small. — length: approximately 1.1 cm on average. — width: approximately 0.7 cm on average. — color as calyx breaks: upper surface: commonly near Yellow Group 6A suffused with near Red Group 48B on the apical part of the petal, basal spot is absent. under surface: commonly near Yellow Group 6B suffused with near Red Group 48C on the apical part of the petal, basal spot is absent.

*Sepals*.—Number: commonly 5. — length: approximately 1.0 cm on average. — width: approximately 0.4 cm on average. — shape: at the top: elongated and narrow, at the base: upright. — extensions: commonly 3 sepals have medium extensions and the other 2 sepals do not. — upper surface: texture: tomentous. color commonly near Yellow-Green Group 144D. — under surface: texture: smooth. color: commonly near Green Group 143A.

*Receptacle*.—Color: commonly near Green Group 143A more or less spotted with near Greyed-Red Group 178A. — length: approximately 0.5 cm on average. — width: approximately 0.4 cm on average. — surface: smooth. — shape: pyriform.

*Peduncle*.—Length: approximately 1.5 cm on average. — width: approximately 0.1 cm on average. — surface: glandular. — color: commonly near Yellow-Green Group 144B.

*Flower*.—Average size when open: approximately between 4.0 to 6.0 cm on average. — shape: flat cup shaped. — shape when viewed from above: irregularly round. — type: semi-double. — number of petals under normal conditions: typically between 7 to 9 petals on average. — petals: shape at the base: acute. shape at the top: rounded and slightly indented. general appearance: obovate. texture: soft. length: approximately 2.0 cm on average. width: approximately 1.0 cm on average. — undulation of the petal: strong. — reflexing of the petal: weak. — petal incision: very weak. — petal arrangement: imbricated with approximately 2 petaloids per flower on average, which are the same shape as the petals but smaller and curved. — petal drop: petals drop off cleanly before drying. — fragrance: none. — color when opening: not applicable, simple flower with very fast opening. — color of the open flower: basal spot on the upper surface: commonly near Yellow Group 6A. upper surface of the flower: commonly near White Group 155D suffused with near Red-Purple Group 62B on the apical part of the petal. basal spot on the under surface: commonly near Yellow Group 6A. under surface of the flower: commonly near White Group 155D suffused with near Red-Purple Group 62C on the apical part of the petal. — discoloration of the fully open flower: yes, the discoloration of the flower goes to white. — anthers: number is 110 on average, length is approximately 0.4 cm on average, coloration is commonly near Yellow-Orange Group 21A, and arrangement is regular around styles. — filaments: length is approximately 0.1 cm on average and coloration is commonly near Yellow-Orange Group 21A. — styles: length is approximately 0.4 cm on average, coloration is commonly near Green-White Group 157A, and number is approximately 8 on average. — stigmas: size is approximately 0.1 cm on average and coloration is commonly near Green-White Group 157A. — pollen: color is commonly near Orange Group 28B and amount is medium to abundant. — hips: size is approximately 0.8 cm on average, coloration is commonly near Yellow-Green Group 144A, and shape is rounded pear shaped.

Development:

*Vegetation*.—Procumbent, semi-glossy, and strong.

*Blooming*.—Early in the season, very abundant and nearly continuous, typically from May to November in France.

*USDA hardiness zone*.—Zone 5.

*Tolerance to disease*.—Good, and particularly against rust (*Phragmidium* sp.).

The new 'MEIJOVAUX' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of rose plant named 'MEIJOVAUX' characterized by the following combination of characteristics:

(a) provides a ground cover growth habit with procumbent vegetation, (b) forms semi-double creamy pink with a creamy yellow center colored flowers, and (c) exhibits a semi-glossy foliage;

substantially as herein shown and described.

* * * * *

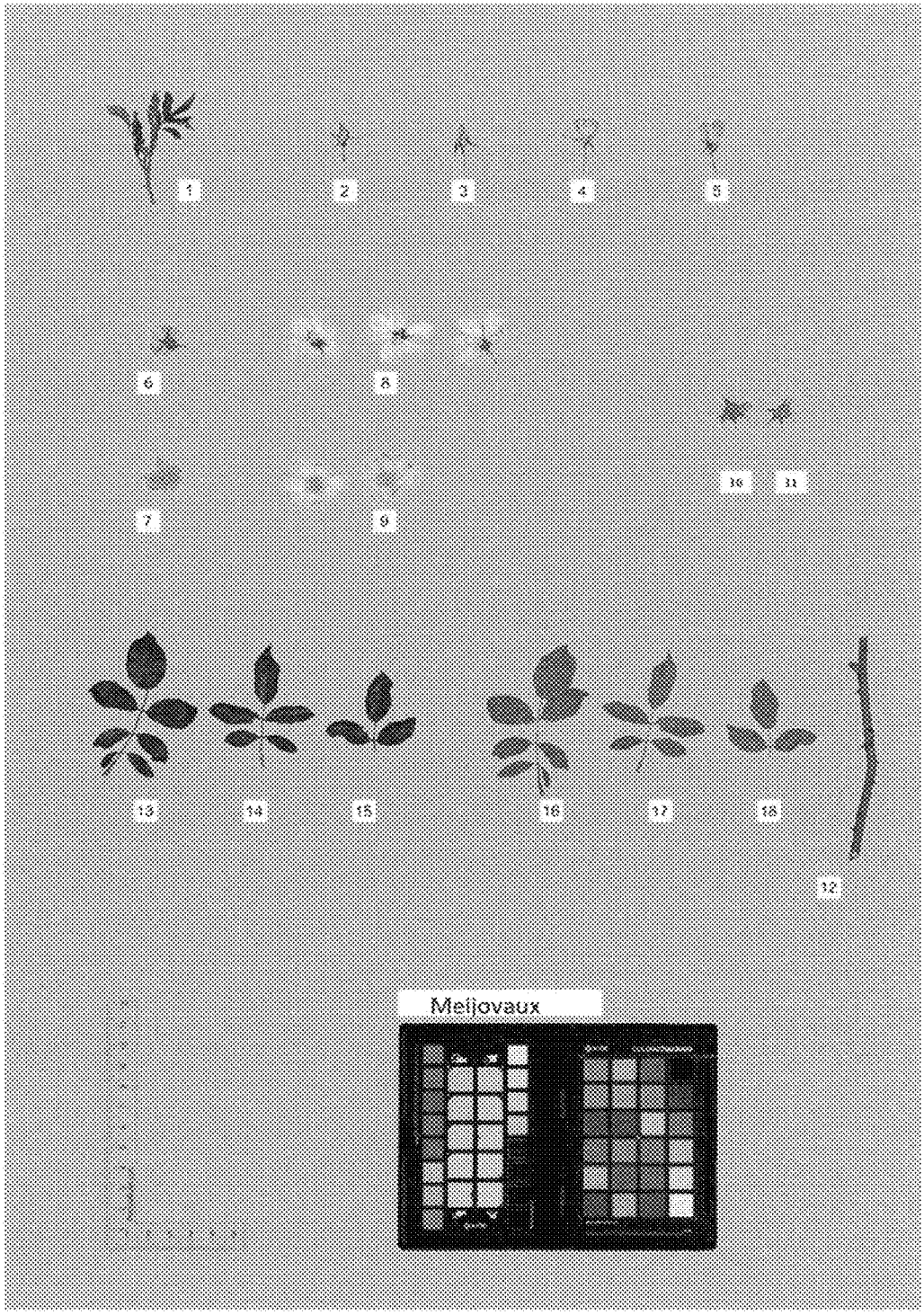
1
2
3
4
5
6
8
7
9
36
31
13
14
15
16
17
18
32
Meijovaux